US006687002B2

(12) United States Patent
Stehle et al.

(10) Patent No.: US 6,687,002 B2
(45) Date of Patent: Feb. 3, 2004

(54) METHOD AND APPARATUS FOR ELLIPSOMETRIC METROLOGY FOR A SAMPLE CONTAINED IN A CHAMBER OR THE LIKE

(75) Inventors: Jean-Louis Stehle, Colombes (FR); Pierre Boher, Yerres (FR)

(73) Assignee: Societe de Production et de Recherches Appliquees, Bois-Colombes (FR)

( * ) Notice: Subject to any disclaimer, the term of this patent is extended or adjusted under 35 U.S.C. 154(b) by 127 days.

(21) Appl. No.: 09/866,503

(22) Filed: May 25, 2001

(65) Prior Publication Data

US 2002/0024668 A1 Feb. 28, 2002

(30) Foreign Application Priority Data

May 26, 2000 (FR) .......................................... 00 06771

(51) Int. Cl.[7] .................................................. G01J 4/00
(52) U.S. Cl. ..................... 356/369; 356/600; 356/632
(58) Field of Search ................................ 356/369, 600, 356/631, 632

(56) References Cited

U.S. PATENT DOCUMENTS

| | | | | |
|---|---|---|---|---|
| 4,198,261 A | * | 4/1980 | Busta et al. ................. 216/60 |
| 4,676,644 A | | 6/1987 | Canteloup .................. 356/351 |
| 5,354,575 A | | 10/1994 | Dagenais et al. ............ 427/10 |
| 5,402,237 A | * | 3/1995 | Rhiger et al. ............... 356/369 |
| 5,764,365 A | | 6/1998 | Finarov ..................... 356/381 |
| 5,940,175 A | * | 8/1999 | Sun ......................... 3556/237.3 |
| 5,969,805 A | * | 10/1999 | Johnson et al. ............... 356/72 |
| 6,304,326 B1 | * | 10/2001 | Aspens et al. ............... 356/369 |
| 6,323,946 B1 | * | 11/2001 | Norton ..................... 356/327 |
| 6,395,563 B1 | * | 5/2002 | Eriguchi ....................... 438/7 |
| 6,469,788 B2 | * | 10/2002 | Boyd et al. .................. 356/369 |

FOREIGN PATENT DOCUMENTS

| | | |
|---|---|---|
| DE | 197 17 885 | 11/1997 |
| DE | 197 23 729 | 12/1998 |
| FR | 2 748 562 | 11/1997 |
| GB | 2 312 952 | 11/1997 |

* cited by examiner

Primary Examiner—Huy Mai
(74) Attorney, Agent, or Firm—Christie, Parker & Hale, LLP

(57) ABSTRACT

An ellipsometric metrology apparatus for a sample contained in a chamber. A light source outside the chamber produces the illuminating beam. A polarizing device outside the chamber polarizes the illuminating beam. A window of selected dimensions and features is disposed in a plane substantially parallel to the sample surface and at least partly closes the chamber. A first directing device directs the polarized illuminating beam on to an area of the sample along a first optical path extending from the polarizing device to the area of the sample through the window. The first optical path forms a predetermined oblique angle of incidence relative to the sample surface. A polarization analyzing device is outside the chamber, a second directing device directs the reflected beam resulting from the illumination of the sample by the illuminating beam on to the analyzing device along a second optical path extending from the sample towards the analyzing device through the window. The reflected beam is symmetrical to the illuminating beam relative to a normal to the sample surface. A detecting device detects the output beam transmitted by the analyzing device in order to supply an output signal processing means processes the output signal in order to determine the changes in stage of polarization in phase and in amplitude caused by the reflection on the area of the sample.

18 Claims, 8 Drawing Sheets

METHOD AND APPARATUS FOR ELLIPSOMETRIC METROLOGY FOR A SAMPLE CONTAINED IN A CHAMBER OR THE LIKE

CROSS-REFERENCE TO RELATED APPLICATION

This application claims priority of French patent Application No. 00 06771, filed on May 26, 2000.

BACKGROUND OF THE INVENTION

The present invention relates to ellipsometric metrology for a sample contained in a chamber or the like in order to obtain measures which are non-destructive of the state of the surface of the sample, without removing the sample from the chamber.

It is applied in general in the optical characterisation of a sample, and more particularly to a sample of thin semi-conducting layers. It is therefore applied in the sequence of production of integrated circuits.

Generally, ellipsometry is used to measure in real time and in-situ a surface change in the course of a manufacturing process of integrated circuits, e.g. during the growth of layers on a substrate.

In a known manner, an ellipsometry apparatus directs a polarised illuminating beam on to a sample at an oblique angle of incidence predetermined with reference to the sample surface. The light beam is reflected by the sample symmetrically relative to a normal to the sample surface. The reflected beam resulting from illumination of the sample is then directed on to a polarisation analysing device, whose output beam is detected before being processed. The changes in state of polarisation in phase and in amplitude brought about by reflection on the sample are processed in order to deduce physical parameters representing the sample.

In practice, the manufacture of integrated circuits comprises a plurality of stages of operation, some of which comprise the depositing of a plurality of successive layers. Most frequently, the depositing of these layers must be carried out without removing the sample from the depositing chamber, in particular in order to avoid breaching the controlled atmosphere of the chamber or contaminating the sample.

It is often necessary to measure physical parameters of one layer before the deposition or processing of the following layer.

A known solution consists in measuring in real time and in-situ the growth of the layers (or the etching) by means of an ellipsometric metrology apparatus.

Such a solution has the disadvantage of demanding as much ellipsometric metrology apparatus as deposition or processing chamber, which makes it relatively expensive.

Moreover, in certain processing stages of the layers (e.g. metal-coating stage), it is difficult or impossible, due to the optical absorption of the layers, to carry out such an ellipsometric solution.

Finally, it is virtually impossible to complete a cartography of the sample without removing the sample from the chamber and/or moving the sample relative to the illuminating beam, which is sometimes difficult to carry out in a chamber due to the limited dimensions of the chamber or the difficulty of incorporating inside the chamber a sample carrier which is movable along the X, Y and/or Z axis.

SUMMARY OF THE INVENTION

The present invention overcomes problems outlined above.

It thus has the main object of integrating an ellipsometric metrology in a chamber, without removing the sample from said chamber in order to measure the sample, e.g. between two manufacturing stages or at the end of one thereof, without contaminating the integrated circuits during manufacture and/or without breaching the controlled atmosphere of the chamber.

To this end, the present invention relates to a method of ellipsometric metrology for a sample contained in a chamber.

According to one important feature of the invention, the method comprises the following stages:

a) to provide a light source outside the chamber to produce an illuminating beam;
b) to provide a polarising device outside the chamber to polarise the illuminating beam;
c) to provide a window of selected dimensions and features and disposed in a plane substantially parallel to the surface of the sample and closing at least partly the chamber;
d) to direct the polarised illuminating beam on to the sample along a first optical path extending from the polarising device to the sample through the window, the first optical path forming a predetermined oblique angle of incidence relative to the sample surface;
e) to produce a reflected beam resulting from the illumination of the sample by the said illuminating beam, the reflected beam being symmetrical to the illuminating beam relative to a normal to the sample surface;
f) to provide a polarisation analysing device outside the chamber;
g) to focus the reflected beam on the analysing device along a second optical path extending from the sample to the analysing device through the window;
h) to detect the output beam emerging from the analysing device in order to supply an output signal;
i) to process the output signal in order to determine the changes in state of polarisation in phase and in amplitude caused by the reflection on the area of the sample.

The method according to the invention thus makes it possible to carry out an ellipsometric measurement of the sample without removing the same from the chamber, which avoids any problems of contamination, in particular during the manufacture of integrated circuits. The method according to the invention also has the advantage of not breaching the controlled atmosphere of the chamber. Moreover, the window permits an operator, if necessary by means of a microscope, to position precisely the illuminating beam on the sample.

The present invention has the further object of an ellipsometric metrology permitting the realisation of a cartography of the sample without removing the same from the chamber and without moving the sample.

To this end, the method according to the invention comprises furthermore a stage j) which consists in keeping the sample fixed in the chamber, and in moving longitudinally and/or laterally the polarised illuminating beam in order to illuminate another area of the sample, and in repeating the stages d) to I) at the same oblique angle of incidence.

The stage j) thus makes it possible to carry out a plurality of ellipsometry steps on a plurality of areas of the sample without moving the sample and without removing the sample from the chamber. Thus a cartography of the sample is obtained without problems of realisation, without causing contamination and without breaching the controlled atmosphere of the chamber.

Advantageously, the stage j) consists furthermore in moving transversely the illuminating beam on the fixed sample, through the window, in order to adjust the distance between the metrology apparatus and the sample surface.

Preferably, the method further comprises a stage of calibration in which the following stages are carried out:

1) to carry out at least a first ellipsometric measurement on a predetermined sample, according to first experimental conditions, without a window,
2) to carry out at least a second ellipsometric measurement on the same sample as that of stage 1), according to second experimental conditions similar to the first experimental conditions, but through the window,
3) to determine from the first and second ellipsometric measurements the effect resulting from the window on the relationship of the tangential amplitudes $\Phi$ of the perpendicular and parallel polarisations of the reflected beam in order to deduce therefrom a correction factor; and
4) to take into account in the processing according to stage I) the correction factor thus deduced.

The present invention also has as an object an ellipsometric metrology apparatus for carrying out the method according to the invention.

A further object of the present invention is a chamber forming a box for holding a sample and comprising an interface with a window of selected dimensions and features disposed in a plane substantially parallel to the sample surface and at least partly closing the box, the box being intended to be associated with a metrology apparatus as described above.

Further features and advantages of the invention will appear from the detailed description below and from the drawings.

BRIEF DESCRIPTION OF THE DRAWINGS

FIG. 10, including

DETAILED DESCRIPTION OF THE PREFERRED EMBODIMENT

The drawings comprise elements of a certain character. As such, they may not only help towards a better understanding of the invention, but also if necessary to define the same.

Figure 1:
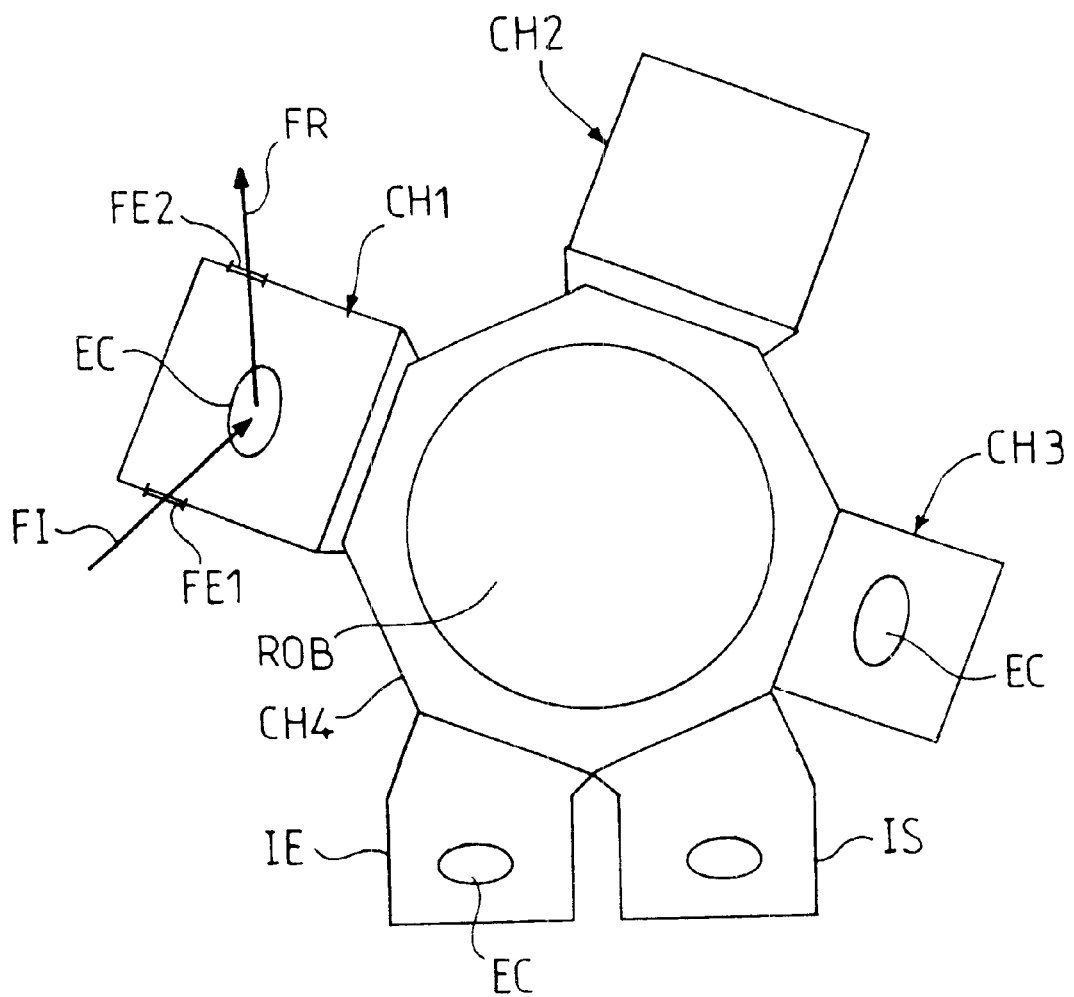
FIG. 1 is a diagrammatic view of a plant for manufacturing integrated circuits equipped with a plurality of chambers for the deposition of layers according to the prior art.

With reference to FIG. 1, a plant for manufacturing integrated circuits of the prior art is shown. The plant comprises a plurality of chambers CH, individually referenced CH1 to CH3, arranged in a star around a transfer chamber CH4. Inside chamber CH4, a robot ROB is capable of introducing or extracting at least one sample EC from one chamber CH to another. The samples EC come from an input interface IE and are directed after processing to an output interface IS.

The chambers CH1 and CH2 are, for example, chambers for the deposition of layers by epitaxy. The chamber CH3 is for example a cooling chamber.

In practice, the atmosphere in the chambers is controlled by equipment well known to the person skilled in the art.

For example, chamber CH1 is equipped with an ellipsometric metrology apparatus of the prior art, of which only the illuminating beam FI and the reflected beam FR on a sample EC are shown. This apparatus is capable of carrying out an ellipsometric measurement to measure in real time and in situ a surface change, e.g. during the growth of a layer on a substrate.

In a known manner, the ellipsometry apparatus directs a polarised illuminating beam on to the sample EC at a predetermined oblique angle of incidence relative to the sample surface. The illuminating beam FI is reflected by the sample in a symmetrical manner relative to a normal to the surface of the sample. The reflected beam FR resulting from the illumination of the sample is then directed to a polarisation analysing device, of which the output beam is detected and then processed. The changes in state of polarisation in phase and in amplitude caused by the reflection on the sample are processed in order to deduce the physical parameters representing the sample.

Windows F1 and F2 are formed in the chamber CH1, on optical paths leading respectively the illuminating beam FI to the chamber CH1 and the reflected beam FR outside the chamber CH1. The windows F1 and F2 are disposed perpendicular to the measurement beam. The angle of incidence must be 60–75° relative to the normal of the sample, which imposes geometric constraints which are often incompatible with certain deposition methods.

With reference to FIG. 1, the ellipsometry is effected during the process of producing layers (growth or etching).

The production of these layers must in general be effected without removing the sample from the deposition chamber and without breaching the controlled atmosphere of the chamber.

It is often necessary to measure physical parameters of a layer before the deposition or production of the following layer.

The ellipsometric solution as shown in FIG. 1 has the disadvantage of requiring as many ellipsometric metrology apparatuses as deposition or layer-producing chambers. Moreover, in certain stages of producing the layers, particularly in the metal-coating stage, it is difficult to effect such an ellipsometric solution in situ. Finally, in order to complete a cartography of the sample, it is appropriate to move the sample relative to the illuminating beam, which is sometimes difficult to effect in a chamber due to the limited dimensions thereof or due to the difficulty of incorporating in the chamber a sample carrier which is mobile along the X, Y and/or Z axis.

It is in this context that the Applicant proposes according to the invention a solution whereby it is possible in particular to effect ellipsometric measurements on a sample without removing said sample from the chamber.

Figure 2:
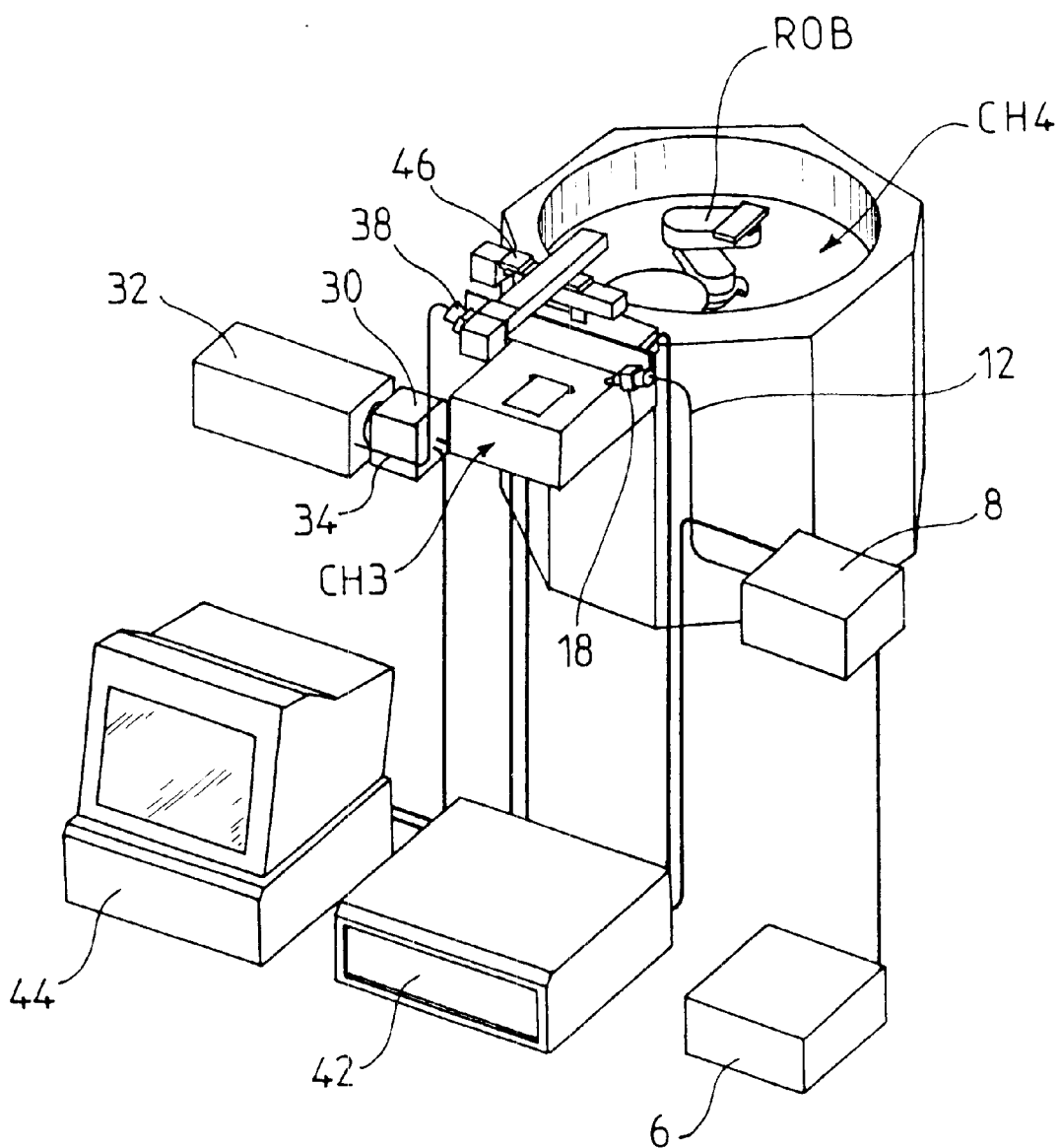
FIG. 2 is a diagrammatic view of an ellipsometric metrology apparatus according to the invention incorporated in a cooling chamber of the plant according to FIG. 1.
Figure 3:
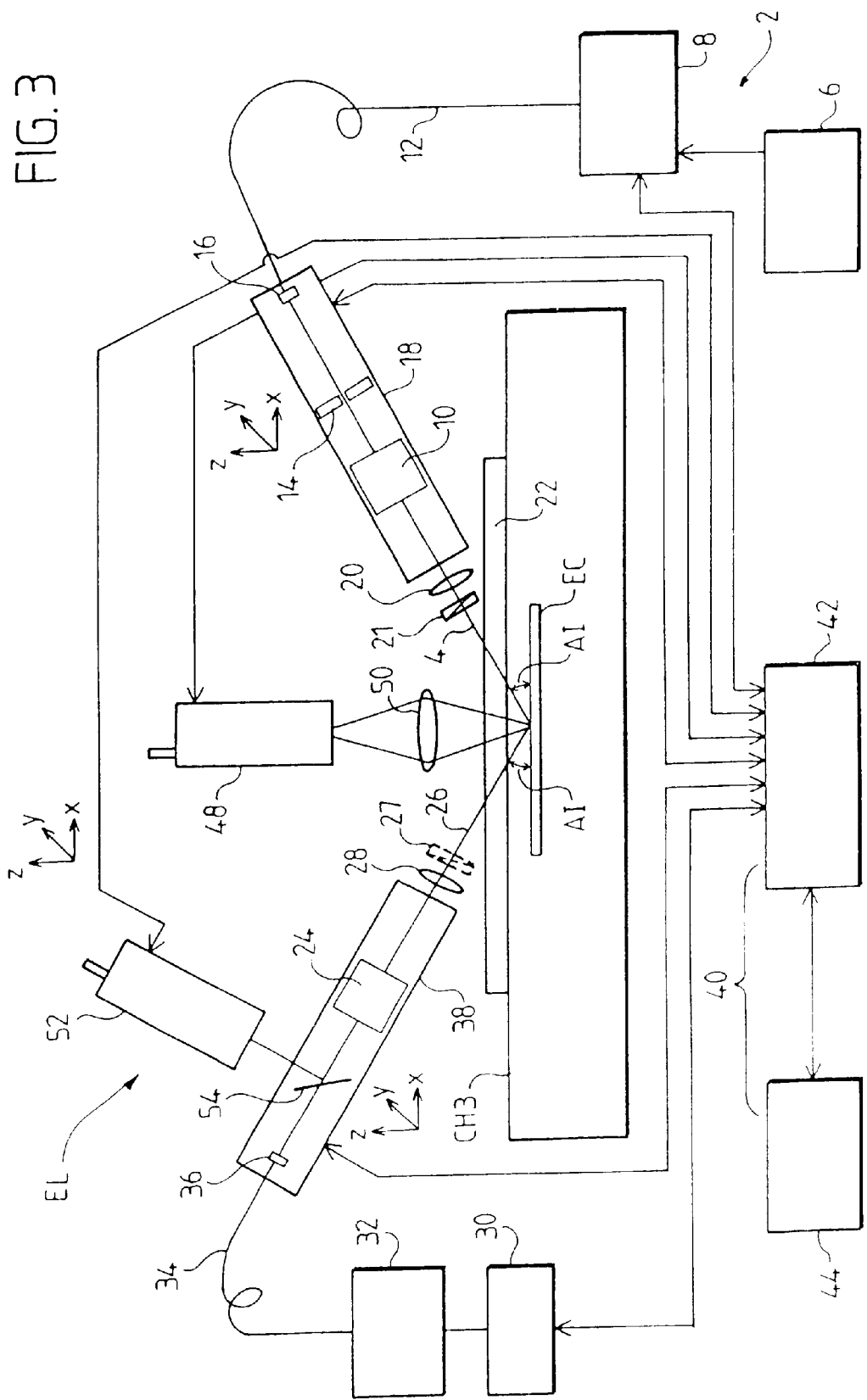
FIG. 3 is another diagrammatic view of the ellipsometric metrology apparatus according to the invention.

With reference to FIGS. 2 and 3, the same chambers CH3 and CH4 are found as in the plant in FIG. 1, as well as the transfer robot ROB.

The ellipsometric metrology apparatus EL according to the invention comprises a light source 2 disposed outside the chamber CH3 in order to produce an illuminating beam 4. The light source 2 comprises a power supply 6 and a lamp 8, e.g. a xenon arc lamp in the case of spectroscopic ellipsometry, or a laser source in the case of monochromatic ellipsometry.

A polarising device 10 is disposed outside the chamber CH3 in order to polarise the illuminating beam 2. The polarising device 10 comprises a Rochon-type polariser for example. The polariser 10 is connected to the lamp 8 by an optic fibre 12. The polarising device 10 comprises a diaphragm 14 mounted upstream of the polariser and downstream of the fibreoptic input coupler 16 in the direction of propagation of light in order to suppress parasitic polarisations of the polariser. The elements 10, 14 and 16 are advantageously housed in an arm 18 forming a lighting head.

The illuminating beam 2 may be directed at the sample EC by focusing means 20 of the microscope objective type. The sample EC is mounted on an object carrier (not shown), preferably fixed.

The chamber CH3 is for example a cooling chamber. It is cuboidal in shape. It is capable of containing samples of different sizes, e.g. of a diameter of 200 millimeters.

The chamber CH3 is at least partly closed by a window 22 of selected dimensions and features disposed in a plane substantially parallel to the sample surface and at least partially closing the chamber.

For example, the dimensions of the window are 130 mm×50 mm×4 mm.

The objective 20 directs the polarised illuminating beam 4 on to an area of the sample, according to a first optical path extending from the lighting head 18 to the area of the sample through the window 22.

A compensating blade 21 may if necessary be interposed between the polariser 10 and the window 22 in order to improve the measurement conditions on certain samples (in particular when phase variation due to the reflection on the sample is +/−90°).

The first optical path forms a predetermined oblique angle of incidence AI relative to the sample surface.

In practice, the angle of incidence AI is of the order of 58°.

A polarisation analysing device 24 is provided outside the chamber CH3.

A reflected beam 26 results from the illumination of the sample by the illuminating beam 4. The reflected beam 26 is directed by an objective 28 on to the analysing device 24 along a second optical path extending from the sample to the analysing device through the window 22.

The reflected beam 26 is symmetrical to the illuminating beam 4 relative to a normal to the surface of the sample.

A compensating blade 27 can be interposed between the window 22 and the analyser 24 in order to have a similar role to that of the blade 21 when the latter is absent.

In the same way, this compensating function may be ensured by a layer of a suitable material (not shown) or of a multi-layer deposition covering the internal and/or external surface of the window. The physical properties of this covering (optical indices, thicknesses) are selected so as to induce a phase variation due to the window of 90° in the usable spectral ranges. This covering is obviously transparent in these spectral ranges (silica, nitride, aluminium).

A detection device 30 of the photodetector type for example, detects the output beam from the analysing device 24 in order to supply an output signal. In the presence of a wide-band light source 2 the photodetector is preceded by a monochromator or spectrometer 32. An optic fibre 34 connects the monochromator or spectrometer 32 to the analysing device 24 by means of an input coupler 36. The elements 24, 36 are advantageously housed in an arm 38 forming an analysing head.

Processing means 40 process the output signal in order to determine the changes in state of polarisation in phase and in amplitude caused by the reflection on the area of the sample. The processing means 40 comprise an electronic control unit 42 and a microcomputer.

The lighting arm 18 and analysing arm 38 are adapted to reduce the size of the metrology apparatus in order to improve its compactness.

The lighting 18 and analysing arms 38 are rigidly connected to a table 46 movable along the X and Y axes in a plane parallel to the sample surface.

This table is used to displace along the X and Y axes the illuminating beam 4 on the sample surface. In practice, the displacement along the X axis is effected along a path of 100 millimeters in length, and the displacement along the Y axis is effected along a shorter path, e.g. of 10 millimeters.

The table 46 is preferably movable along the Z axis in order to adapt the distance between the illumination and analysis arms and the sample surface. This adaptation is useful in the case of an illumination spot of small dimensions relative to the precision of displacement of the table.

The angle of incidence AI is for example fixed after a calibration stage around 58°.

An image recognition device 48, of the CCD camera type, comprising a lens 50, is also provided to take images of the sample at a right angles to the surface of the sample. Preferably, this device 48 is rigidly connected to the mobile table.

In the same way, an autofocusing device 52, of the CCD camera type, intercepts by means of a separator 54 the signal transmitted by the analyser 24 in order to adapt the autofocus of the apparatus. Preferably, this device 52 is also rigidly connected to the mobile table.

The electronic control unit 42 pilots in particular the displacement along the X, Y and Z axis of the table 46 in order to displace the elements 18, 38, 48 and 52. The unit 42 also controls the elements 8 and 30.

One of the main features of the metrology device according to the invention is in the plane window 22 disposed in a plane parallel to that of the sample surface, and closing at least partially the chamber containing the sample, the illuminating arms 18 and analysing arms 38 being disposed outside the chamber.

When the illuminating arms 18 and analysing arms 38 are disposed in a configuration known as "straight line", the tests show that the ellipsometric metrology apparatus functions correctly when the tangent parameter psi (Ψ) is equal to 1+/−0.01 and when the cosine parameter delta ( )) is equal to 1+/−0.01 in the wavelength range 0.25 nm to 0.85 nm.

The Applicant has made calculations to determine the effect of the window on the calculation of ellipsometric parameters, in particular tangent psi and cosine delta.

Figure 4:
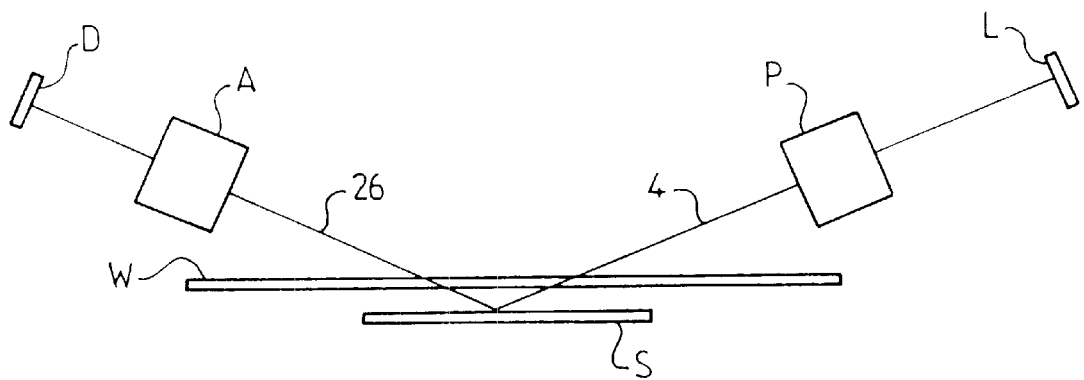
FIG. 4 shows diagrammatically the essential elements of the ellipsometric metrology apparatus according to the invention.

With reference to FIG. 4, the essential elements of the apparatus which take part in calculation are found again, with $E_I$ for the source, P for the polariser, W for the window, S for the sample, A for the analyser, and D for the detector.

The equation 1 attached gives the electric field $E_D$ on the detector.

The equation 2 attached expresses as a matrix the electric field $E_D$ on the detector.

The equation 3 attached expresses the intensity I without the window. The coefficients κ, ∀ and ∃ of the equation 3 are given respectively in the equations 4, 5 and 6 attached in the annex.

In general, the tangent parameter psi and cosine delta parameter are expressed respectively according to the equations 7 and 8 attached.

When the window is placed between the sample and the illumination and analysis arms, the matrix calculation is expressed according to the equation 9 attached, which makes it possible to express the tangent parameter psi and the cosine parameter delta with or without the window according to the equations 10 and 11 attached.

Figure 5:
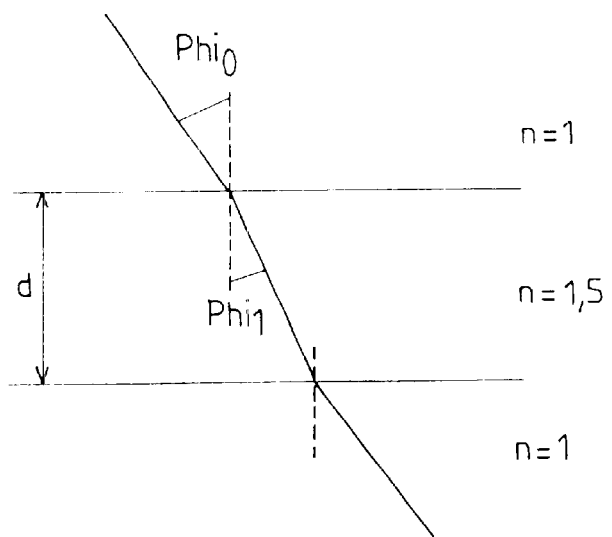
FIG. 5 shows diagrammatically the optical path of the illuminating beam through a window closing a chamber according to the invention at least partly.

With reference to FIG. 5, the optical path has been shown of the illuminating beam or of the reflected beam through a window. The Applicant has for example evaluated the effect of a window of the PUROPSIL (registered Trade Mark) type of a thickness d of 4 mm an of a coefficient n (e.g. n=1.5).

The transmission T of the window is given in the equation 12 in which the coefficients $t_{01}$, $t_{10}$, $r_{01}$ and $r_{10}$ are the coefficients of Fresnel corresponding to the coefficients of transmission and reflection at the ambient/window interface and ambient window (equations 13, 14, 15 and 16). The parameter δ represents the phase shift due to the window thickness (equation 17).

The product of the coefficients $t_{01}*t_{10}$ is expressed in the attached equation 18.

The two coefficient a and b of the matrix expressed in the equation 9 are given respectively in the equations 19 and 20.

The correction factor intended to be applied to the parameter tangent psi is given with reference to the equation 21. The equation 22 expresses the correction factor to be applied to the phase shift.

It therefore appears from the theoretical calculations (in a straight line) that the parameter tangent psi must be corrected by a selected factor, substantially depending on the wavelength (through the slight variation of the index of refraction of the window as a function of the wavelength) whereas the cosine parameter delta is not affected by the window.

Figure 6:
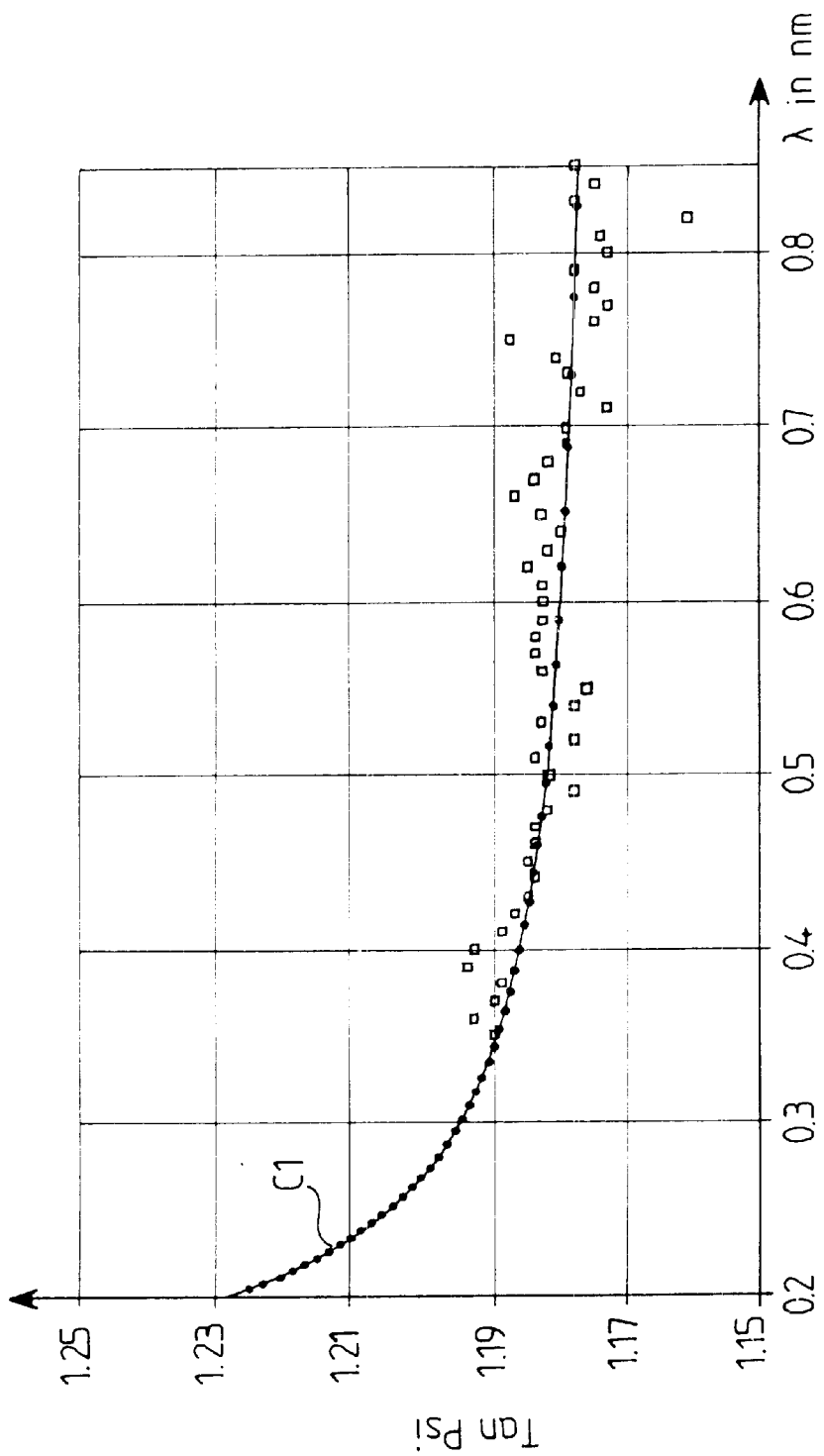
FIG. 6 shows a curve of the tangent parameter psi, measured as a straight line through a window inclined at 58° as a function of the wavelength.

With reference to FIG. 6, the point values of the tangents psi measured as a function of the wavelength have been shown with an ellipsometry in a straight line and a window inclined at 58°. These points measured are to be compared with the curve C1, which expresses the calculation of the parameter tangent psi according to the equations mentioned above, with a PUROPSIL window.

It should be noted that the correction factor expressed in the equation 21 must be applied twice due to the double passage through the window (illumination and reflection).

Figure 7:
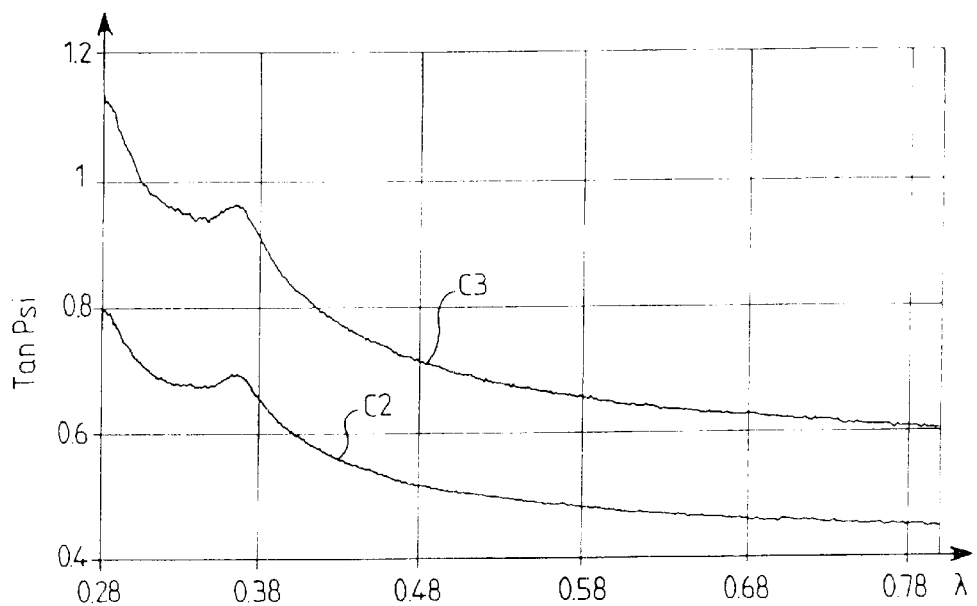
FIG. 7 shows measurement curves of the tangent parameter psi on a silicon substrate with or without window as a function of the wavelength.
Figure 8:
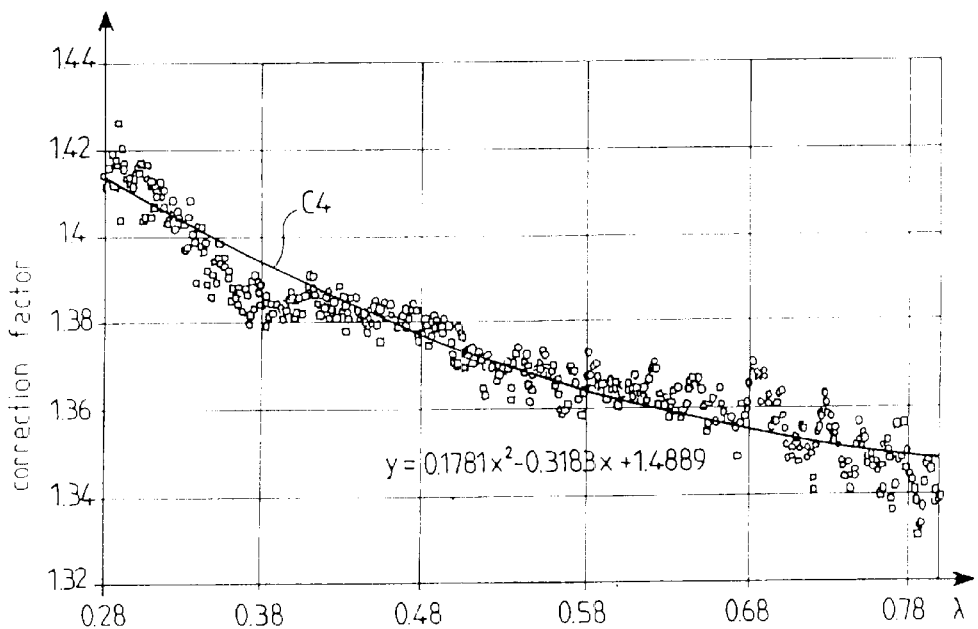
FIG. 8 shows a curve of the correction factor resulting from the effect of the window to be applied to the tangent parameter psi measured as a function of the wavelength.

In theory, the calibration of the effect of the window can be realised in a straight line with a window inclined at an incidence of for example 58°. But in practice, the correction factor should be evaluated on the parameter tangent Φ, using the ratio (curve C4 in FIG. 8) of two measures of tangent psi (FIG. 7), one (curve C2) measured without window and the other (curve C3) measured with window (FIG. 7), on a sample in a measuring position and after adjustment of the optical elements.

In practice, the calibration stage comprises the following stages:

1) to carry out at least a first ellipsometric measurement on a predetermined sample according to first experimental conditions, without a window:
2) to carry out at least a second ellipsometric measurement on the same sample as that of stage 1) according to second experimental conditions generally similar to the first experimental conditions but through the window;
3) to determine from the first and second ellipsometric measurements the effect resulting from the window on the relationship of the tangent amplitudes φ of the perpendicular and parallel polarisations of the reflected beam in order to deduce a correction sector; and
4) to take into account in the processing according to the preceding stage the correction factor thus deduced.

The polynomial approximation (FIG. 8) can be used directly to correct the measurements on other examples.

A cartography can be realised by virtue of the invention. The cartography consists in keeping the sample fixed in the chamber, in displacing longitudinally and/or laterally the polarised illuminating beam in order to light up another area of the sample, and in repeating the different stages of the process according to the same oblique angle of incidence, which makes it possible to carry out a plurality of ellipsometric measurements on a number of zones of the sample without moving the sample and without removing the sample from the chamber.

The method comprises furthermore a stage which consists in moving transversely the illuminating beam on the fixed sample through the window in order to adjust the distance between the metrology apparatus and the sample surface.

Figure 9:
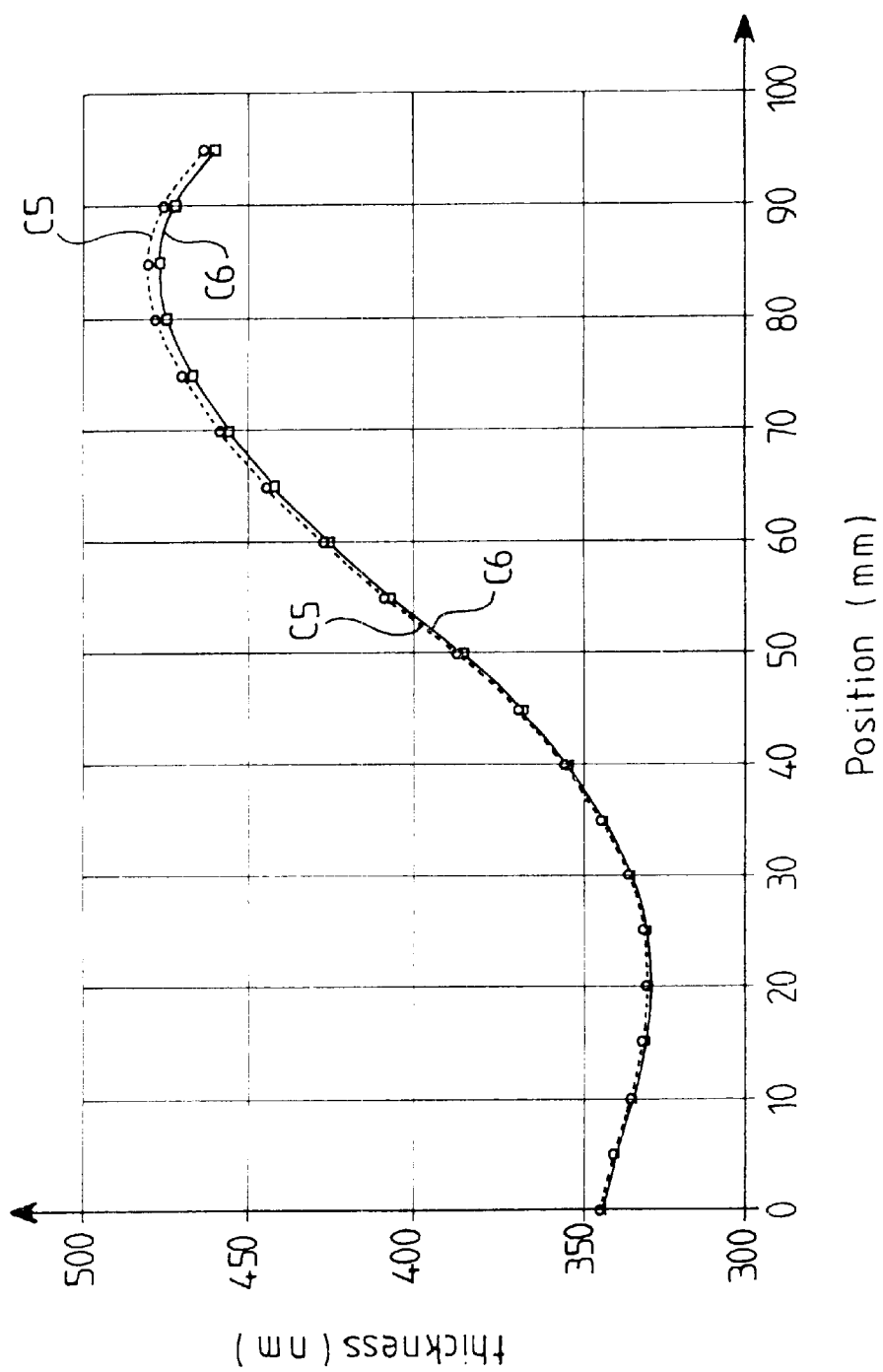
FIG. 9 shows a curve of the silicon thickness measured on a silicon substrate with or without window on a large diameter of the sample.

With reference to FIG. 9, measurements of thickness have been shown in nm of a sample comprising one layer of silica on a silicon substrate having a radius of 100 mm. The curve C5 represents the measurements effected without a window whereas the curve C6 shows the measurements effected with a window (and corrected according to the correction factor described above). The good match between the two curves shows that the cartography of the sample through the window according to the invention on an axis X of 100 mm is totally coherent with the same measurement carried out without a window.

As a modification, the window can be divided into first and second windows of identical dimensions and features and selected to permit the respective passage of illuminating and reflected beams.

The chamber is for example a cooling chamber adapted for a production line for integrated circuits in order to receive samples to be measured discharged from a production chamber of the production line.

Figure 10A:
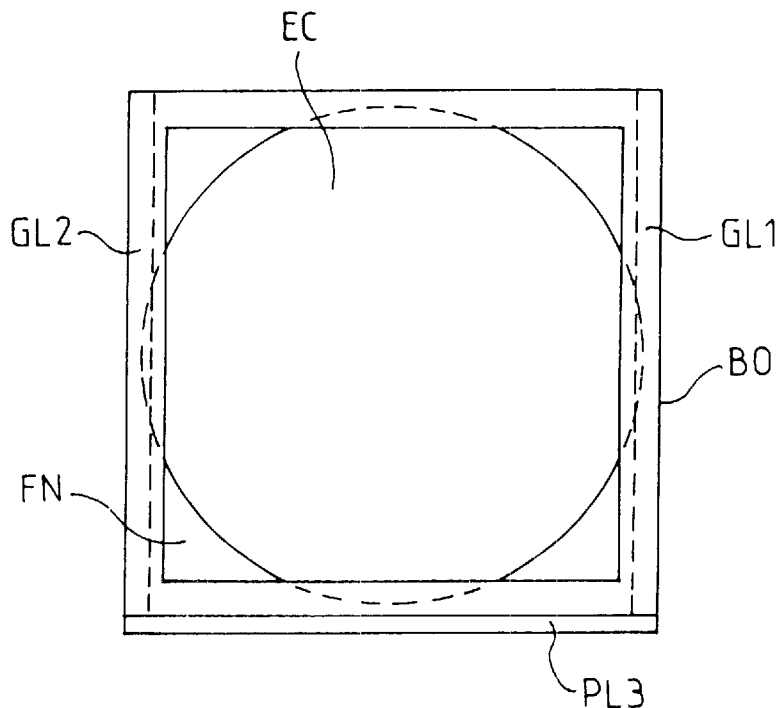
FIGS. 10A, 10B, and 10C, shows diagrammatically a box forming a chamber containing a sample and capable of being adapted to the metrology apparatus according to the invention.
Figure 10B:
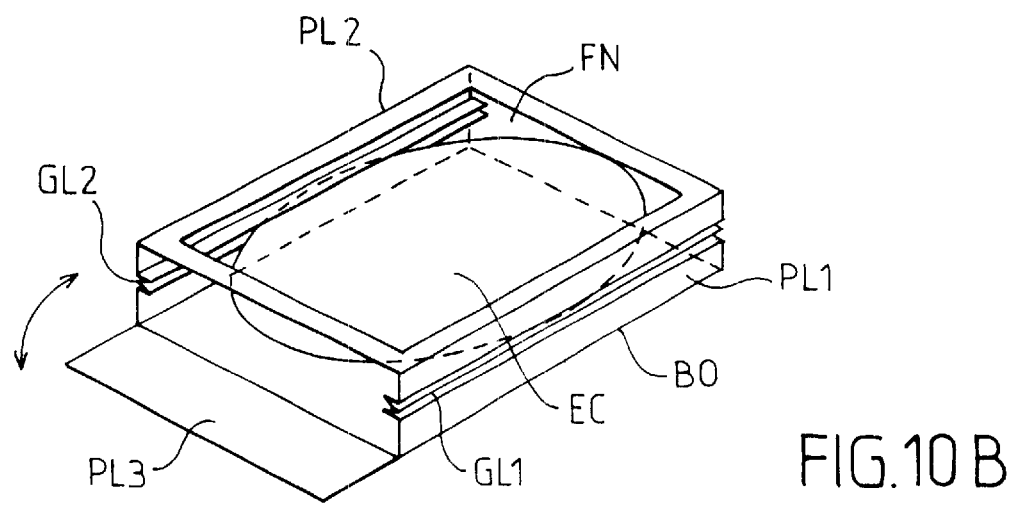
Figure 10C:
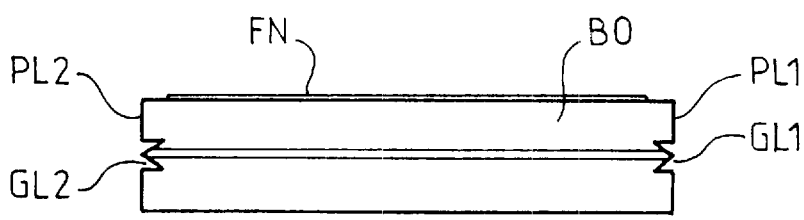

As a modification (FIGS. 10A to 10C), the chamber can be a box BO forming a sample carrier capable of containing a sample EC and of being loaded with or relieved of the sample on the metrology apparatus described above.

For example, the box BO is cuboidal. It has two longitudinal walls PL1 and PL2 each equipped with a slide GL1, GL2 for holding the sample EC inside the box BO. The box further comprises a lateral folding wall PL3 permitting the loading/unloading of the sample in/from the box. According to the invention, the box comprises an upper face equipped with a window FN closing the box.

It should be noted that the window according to the invention can also have the function of providing thermal insulation, in particular in the case of ellipsometric measurements carried out in a thermally controlled environment (oven, cryostat).

It should be noted also that the window according to the invention can be used also to insulate the outside air environment and a liquid environment inside the chamber. This window avoid the well known problems of measuring samples inside a liquid related to the planicity and the vibrations. This can have a big interest for the measurement of biocaptors in wet Environment, as well as wafers during wet process, as etch, clean, . . . . In this case the modelling will take the water medium into account.

TABLE 1

| | |
|---|---|
| $E_d^s = A^* R(A)^* W^* S^* W^* R(-P)^* P^* E_L$ | Equation 1 |
| $E_d^{10} = \begin{bmatrix} 1 & 0 \\ 0 & 0 \end{bmatrix} * \begin{bmatrix} \cos A & -\sin A \\ \sin A & \cos A \end{bmatrix} * \begin{bmatrix} a & 0 \\ 0 & b \end{bmatrix} * \begin{bmatrix} r_p & 0 \\ 0 & r_s \end{bmatrix} *$ $\begin{bmatrix} a & 0 \\ 0 & b \end{bmatrix} * \begin{bmatrix} \cos P & \sin P \\ -\sin P & \cos P \end{bmatrix} * \begin{bmatrix} 1 & 0 \\ 0 & 0 \end{bmatrix} * \begin{bmatrix} E_0 \\ E_0 \end{bmatrix}$ | Equation 2 |
| $I = E_d^* E_d^* = K(1 + \alpha \cos 2P + \beta \sin 2P)$ | Equation 3 |
| $K = \dfrac{E_0^2 |r_s|^2}{2} * \dfrac{\cos^2 A}{\frac{|r_p|^2}{|r_s|^2} + \tan^2 A}$ | Equation 4 |
| $\alpha = \dfrac{\frac{|r_p|^2}{|r_s|^2} - \tan^2 A}{\frac{|r_p|^2}{|r_s|^2} + \tan^2 A}$ | Equation 5 |
| $\beta = \dfrac{2\tan A \cos(\delta_p - \delta_s) \frac{|r_p|}{|r_s|}}{\frac{|r_p|^2}{|r_s|^2} + \tan^2 A}$ | Equation 6 |
| $\Delta = \delta_p - \delta_s$ | Equation 7 |
| $\tan \Psi = \dfrac{|r_p|}{|r_s|}$ | Equation 8 |
| $\begin{bmatrix} a & 0 \\ 0 & b \end{bmatrix} * \begin{bmatrix} r_p & 0 \\ 0 & r_s \end{bmatrix} * \begin{bmatrix} a & 0 \\ 0 & b \end{bmatrix}$ | Equation 9 |
| $\tan \Psi^{\text{with}} = \left[\dfrac{|a|}{|b|}\right]^2 * \tan \Psi^{\text{without}}$ | Equation 10 |
| $\cos \Delta^{\text{with}} = \cos(\Delta^{\text{without}} - 2(\delta_a - \delta_b))$ | Equation 11 |
| $T = \dfrac{t_{01} t_{10} e^{-j\beta}}{1 + r_{01} r_{10} e^{-2j\beta}} = t_{01} t_{10} e^{-j\delta}$ | Equation 12 |
| $t_{01}^p = \dfrac{2\cos\varphi_0}{n\cos\varphi_0 + \cos\varphi_1}$ | Equation 13 |

TABLE 1-continued

| | |
|---|---|
| $t_{01}^s = \dfrac{2\cos\varphi_0}{\cos\varphi_0 + n\cos\varphi_1}$ | Equation 14 |
| $r_{01}^p = \dfrac{n\cos\varphi_0 - \cos\varphi_1}{n\cos\varphi_0 + \cos\varphi_1}$ | Equation 15 |
| $\beta = 2\pi \left[\dfrac{d}{\lambda}\right] \sqrt{n^2 - \sin^2 \varphi_0}$ | Equation 17 |
| $t_{01} * t_{10} = 1 - r_{01}^2$ | Equation 18 |
| $a = (1 - r_{01p}^2) e^{-j\beta}$ | Equation 19 |
| $b = (1 - r_{01s}^2) e^{-j\beta}$ | Equation 20 |
| $\left[\dfrac{|a|}{|b|}\right]^2 = \left[\dfrac{1 - r_{01p}^2}{1 - 4_{01s}^2}\right]^2$ | Equation 21 |

What is claimed is:

1. A method of ellipsometric measurement for a sample contained in a chamber, comprising the steps of:
   a) providing a light source outside the chamber to produce an illuminating beam;
   b) providing a polarising device outside the chamber to polarise the illuminating beam;
   c) providing a window of selected dimensions and features disposed in a plane substantially parallel to the sample surface and closing the chamber at least partially;
   d) directing the polarised illuminating beam on to an area of the sample, along a first optical path extending from the polarising device to the area of the sample through the window, the said first optical path forming a predetermined oblique angle of incidence relative to the sample surface;
   e) producing a reflected beam resulting from the illumination of the area of the sample by the illuminating beam, the reflected beam being symmetrical to the illuminating beam relative to a normal to the sample surface;
   f) providing a polarisation analysing device outside the chamber;
   g) directing the reflected beam on to the analysing device along a second optical path extending from the sample to the analysing device through the window;
   h) detecting the output beam transmitted by the analysing device to supply an output signal;
   i) processing the output signal in order to determine the changes in state of polarisation in phase and in amplitude caused by the reflection on to the area of the sample; and
   j) a calibration stage comprising the following steps:
      1) carrying out a first ellipsometric measurement on a predetermined sample, according to first experimental conditions without a window,
      2) effecting a second ellipsometric measurement on the same sample as that in step 1) according to second experimental conditions similar to the first experimental conditions, but through the window,
      3) determining from the first and second ellipsometric measurements the effect resulting from the window on the relationship of the tangent Ψ amplitudes of the perpendicular and parallel polarisations of the reflected beam in order to deduce therefrom a correction factor, and 4) processing according to step i) for deducing a correction factor.

2. The method claim 1, further comprising the step of j) keeping the sample fixed in the chamber, moving longitudinally and/or laterally the polarised illuminating beam in order to light up another area of the sample, and repeating steps d) to i), at the same oblique angle of incidence, which makes it possible to effect a plurality of ellipsometry measurements on a plurality of areas of the sample, without moving the sample and without removing the sample from the chamber.

3. The method of claim 2, wherein the step j) further comprises displacing transversely the illuminating beam on the fixed sample through the window in order to adjust the distance between the metrology apparatus and the sample surface.

4. An ellipsometric metrology apparatus for a sample contained in a chamber, comprising:

a light source outside the chamber for producing an illuminating beam;

a polarising device outside the chamber for polarising the illuminating beam;

a window of selected dimensions and features disposed in a plane substantially parallel to the sample surface and at least partly closing the chamber;

a first directing device for directing the polarised illuminating beam on to an area of the sample along a first optical path extending from the polarising device to the area of the sample through the window, the first optical path forming a predetermined oblique angle of incidence relative to the sample surface;

a polarisation analysing device outside the chamber;

a second directing device for directing the reflected beam resulting from the illumination of the sample by the illuminating beam on to the analysing device along a second optical path extending from the sample towards the analysing device through the window, the reflected beam being symmetrical to the illuminating beam relative to a normal to the sample surface;

a detecting device for detecting the output beam transmitted by the analysing device in order to supply an output signal;

processing means for processing the output signal in order to determine the changes in stage of polarisation in phase and in amplitude caused by the reflection on the area of the sample; and j) means for calibration comprising:

1) means for carrying out a first ellipsometric measurement on a predetermined sample, according to first experimental conditions without a window, 2) means for effecting a second ellipsometric measurement on the same sample as that in step 1) according to second experimental conditions similar to the first experimental conditions, but through the window, 3) means for determining from the first and second ellipsometric measurements the effect resulting from the window on the relationship of the tangent Ψ amplitudes of the perpendicular and parallel polarisations of the reflected beam in order to deduce therefrom a correction factor, and 4) means for processing according to step i) for deducing a correction factor.

5. The apparatus of claim 4, further comprising displacement means for displacing longitudinally and/or laterally the polarised illuminating beam in order to light up another area of the sample, at the same oblique angle of incidence, which makes it possible to obtain a cartography of the sample without moving the sample and without removing the sample from the chamber.

6. The apparatus of claim 5, wherein the displacement means comprise a table which is adjustable along the X and/or Y and/or Z axis.

7. The apparatus of claim 6, wherein the table is capable of carrying the polarising device, the analysing device and the first and second directing devices.

8. The apparatus of claim 7, further comprising a first optic fibre disposed between the light source and the polarising device.

9. The apparatus of claim 7, further comprising a second optic fibre disposed between the analysing device and the detection device.

10. The apparatus of claim 4, wherein the window comprises first and second windows of identical dimensions and features and selected to permit the respective passage of the illuminating and reflected beams.

11. The apparatus of claim 4, wherein the displacement means are capable of displacing transversely the illuminating beam on the fixed sample, which makes it possible to adjust the distance between the metrology apparatus and the sample surface.

12. The apparatus of claim 4, further comprising a diaphragm disposed upstream of the polarising device in the direction of propagation of light.

13. The apparatus according to claim 4, further comprising a compensating blade interposed between the polariser and the window.

14. The apparatus according to claim 4, further comprising a compensating blade interposed between the window and the analyser.

15. The apparatus according to claim 4, further comprising a layer of a suitable material covering the internal and/or external surface of the window.

16. The apparatus according to claim 4, wherein the chamber is a cooling chamber capable of being adapted to a production line for integrated circuits, in order to receive samples to be measured coming from the said production line.

17. The apparatus according to claim 4, wherein the chamber is a box forming a sample-carrier capable of containing a sample and comprising an interface connected to the metrology apparatus.

18. A box capable of containing a sample and being intended to be associated with a metrology apparatus, comprising:

an upper face with a window of selected dimensions and features disposed in a plane substantially parallel to a sample surface and closing the box;

a light source outside the chamber in order to produce an illuminating beam;

a polarising device outside the chamber in order to polarise the illuminating beam;

a first directing device for directing the polarised illuminating beam on to an area of the sample along a first optical path extending from the polarising device to the area of the sample through the window, the first optical path forming a predetermined oblique angle of incidence relative to the sample surface;

a polarisation analysing device outside the chamber;

a second directing device for directing the reflected beam resulting from the illumination of the sample by the illuminating beam on to the analysing device along a second optical path extending from the sample towards the analysing device through the window, the reflected beam being symmetrical to the illuminating beam relative to a normal to the sample surface;

a detection device for detecting the output beam transmitted by the analysing device in order to form an output signal;

processing means for processing the output signal in order to determine the changes in stage of polarisation in phase and in amplitude caused by the reflection on the area of the sample; and j) means for calibration comprising:
  1) means for carrying out a first ellipsometric measurement on a predetermined sample, according to first experimental conditions without a window,
  2) means for effecting a second ellipsometric measurement on the same sample as that in step 1) according to second experimental conditions similar to the first experimental conditions, but through the window,
  3) means for determining from the first and second ellipsometric measurements the effect resulting from the window on the relationship of the tangent $\Psi$ amplitudes of the perpendicular and parallel polarisations of the reflected beam in order to deduce therefrom a correction factor, and
  4) means for processing according to step i) for deducing a correction factor.

* * * * *

UNITED STATES PATENT AND TRADEMARK OFFICE
CERTIFICATE OF CORRECTION

PATENT NO. : 6,687,002 B2
DATED : February 3, 2004
INVENTOR(S) : Jean-Louis Stehle et al.

It is certified that error appears in the above-identified patent and that said Letters Patent is hereby corrected as shown below:

Column 11,
Line 50, delete "j)"
Line 65, delete "step i)", insert -- processing the output signal --

Column 14,
Line 1, delete "j)"
Line 15, delete "step i)", insert -- processing the output signal --

Signed and Sealed this

Twenty-eighth Day of June, 2005

JON W. DUDAS
*Director of the United States Patent and Trademark Office*